(12) United States Patent
Kim et al.

(10) Patent No.: US 8,697,441 B2
(45) Date of Patent: Apr. 15, 2014

(54) METHOD OF INDUCING HIGH ACTIVITY OF HUMAN ADIPOSE STEM CELL AND MEDIUM THEREFOR

(75) Inventors: Hyo Soo Kim, Seoul (KR); Hyun Jae Kang, Seoul (KR); Eun Ju Lee, Seoul (KR)

(73) Assignee: Seoul National University Hospital, Seoul (KR)

( * ) Notice: Subject to any disclaimer, the term of this patent is extended or adjusted under 35 U.S.C. 154(b) by 0 days.

(21) Appl. No.: 13/510,528

(22) PCT Filed: Oct. 8, 2010

(86) PCT No.: PCT/KR2010/006911
§ 371 (c)(1),
(2), (4) Date: Oct. 10, 2012

(87) PCT Pub. No.: WO2011/043629
PCT Pub. Date: Apr. 14, 2011

(65) Prior Publication Data
US 2013/0023048 A1    Jan. 24, 2013

(30) Foreign Application Priority Data
Oct. 8, 2009    (KR) ........................ 10-2009-0095403

(51) Int. Cl.
*C12N 5/071* (2010.01)
(52) U.S. Cl.
USPC ........................................................ 435/366
(58) Field of Classification Search
None
See application file for complete search history.

(56) References Cited

PUBLICATIONS

Sugiyama et al., Glycerol Suppresses Proliferation of Rat Hepatocytes and Human HepG2 Cells, Journal of Surgical Research 103, 236-242 (2002).*
Flynn et al., "Proliferation and Differentiation of Adipose-Derived Stem Cells on Naturally Derived Scaffolds," Biomaterials 29:1862-1871, 2008.
Gomillion et al., "Stem Cells and Adipose Tissue Engineering," Biomaterials 27:6052-6063, 2006.
Jeon et al., "Sphingosylphosphorylcholine Induces Proliferation of Human Adipose Tissue-Derived Mesenchymal Stem Cells via Activation of JNK," J. Lipid Res. 47:653-664, 2006.
Zaminy et al., "Effects of Melatonin on the Proliferation and Differentiation of Rat Adipose-Derived Stem Cells," Indian J. Plast. Surg. 41:8-14, 2008.
International Search Report from PCT/KR2010/006911, dated Jun. 17, 2011 (date of mailing of report) and Jun. 16, 2011 (date of completion of search).

\* cited by examiner

*Primary Examiner* — Suzanne M Noakes
*Assistant Examiner* — Stephen Chong
(74) *Attorney, Agent, or Firm* — Clark & Elbing LLP (57) ABSTRACT

The present invention relates to a method of inducing high activity of human adipose stem cells, highly active stem cells induced by the method, cell therapeutic agents including the highly active stem cells, and a medium for inducing high activity of human adipose stem cells. The method of the present invention enables a long-term culture of human adipose stem cells while maintaining high activity, production yield and differentiation potency of the stem cells through in vitro culture, even in case culture conditions are not appropriate for mature human adipocytes, security of adipocytes is not guaranteed, or adipocytes are diseased.

6 Claims, 12 Drawing Sheets

Without Adipocyte-expose

With Adipocyte-expose

Adipose stem cells
NOT exposed to glycerol

Adipose stem cells
exposed to glycerol

METHOD OF INDUCING HIGH ACTIVITY OF HUMAN ADIPOSE STEM CELL AND MEDIUM THEREFOR

CROSS-REFERENCE TO RELATED APPLICATIONS

This application is the U.S. national stage filing under 35 U.S.C. §371 of international application PCT/KR2010/006911, filed Oct. 8, 2010, which claims priority from Korean Patent Application 10-2009-0095403, filed Oct. 8, 2009.

TECHNICAL FIELD

The present disclosure relates to a method for inducing high activity of human adipose stem cells and a medium therefor, more particularly to a method of inducing high activity of human adipose stem cells, highly active stem cells induced by the method, cell therapeutic agents including the highly active stem cells, and a medium for inducing high activity of human adipose stem cells.

BACKGROUND ART

Stem cells are cells that can differentiate into various cell types constituting the tissues of an organism, and collectively refer to the cells in an undifferentiated state that can be obtained from embryonic, fetal and adult tissues. The stem cells differentiate into specific cell types under necessary stimulation (environment). Unlike the differentiated cells whose cell division has stopped, they can produce the cells identical to themselves through cell division (self-renewal) and thus can proliferate (expansion). Also, they can differentiate into other cells under different environment or stimulation (plasticity).

Largely, the stem cells are divided into embryonic stem cells (ES cells), which are isolated from the embryo and have the totipotency or pluripotency of differentiating into all cell types, and adult stem cells, which are isolated from the individual cells have multipotency. The inner cell mass during the early embryogenic stage of blastocyte is the mass of cells that will eventually give rise to the structures of the fetus. Theoretically, the embryonic stem cells derived from the inner cell mass have the potential of differentiating into any cell type of the organism. That is to say, the embryonic stem cells are undifferentiated cells that can proliferate infinitely, differentiate into all cell types, and pass their genetic inheritance to the next generation by producing germ cells unlike the adult stem cells.

Human embryonic stem cells are obtained by isolating and culturing the inner cell mass during the formation of human embryo (blastocyst). Currently, the human embryonic stem cells obtained worldwide are derived from the frozen embryos remaining after sterilization. The cells have the totipotency of differentiating into any cell type, can be cultured in immortal, undifferentiated state, and can pass their genetic inheritance to the next generation by producing germ cells (Thomson et al., *Science,* 282: 1145-1147, 1998; Reubinoff et al., *Nat. Biotechnol.,* 18: 399-404, 2000).

Although various attempts have been made to utilize the human embryonic stem cells capable of differentiating into various cells as cell therapeutic agents, the obstacles of canceration and immune rejection remain to be solved.

Recently, use of mesenchymal stem cells having immunomodulatory function has been proposed to solve these problems. The mesenchymal stem cells are multipotent cells that can differentiate into adipocytes, osteocytes, chondrocytes, myocytes, neurons and cardiomyocytes and are reported to have the immunomodulatory function. Although they can be isolated from various tissues, their abilities differ slightly and surface markers are also different depending on their origin. At present, the mesenchymal stem cells are defined by the ability to differentiate into osteocytes, chondrocytes and myocytes, the spiral shape, and the expression of the surface markers CD73(+), CD105(+), CD34(−) and CD45(−).

The minimum number of cells required for cell therapy or regenerative medicine is around $1 \times 10^9$. Considering the experiments necessary for establishment of conditions and setup of references, the number increases further.

To supply mesenchymal stem cells of various origins in that amount, at least 10 subculturing passages are required in vitro. Then, the cells are no more appropriate for therapy because they become aged and deformed. This is one of the problems of the current system for culturing mesenchymal stem cells. Even when the conditions and references are determined using the cells, the cells may have been depleted already and mesenchymal stem cells from a different person may have to be used. In that case, experiments should be carried out again for the cells. Accordingly, a new method capable of solving these problems is necessary to use the mesenchymal stem cells as cell therapeutic agents.

Korean Patent Publication No. 2005-0032020 discloses adipose-derived stem cells and lattices, and Korean Patent No. 0821128 discloses a method and a system for preparing stem cells from fat tissue.

Throughout the specification, a number of publications and patent documents are referred to and cited. The disclosure of the cited publications and patent documents is incorporated herein by reference in its entirety to more clearly describe the state of the related art and the present disclosure.

DISCLOSURE

Technical Problem

The present disclosure is directed to solving the above-described problems and providing a method of inducing high activity of human adipose stem cells necessary for cell therapy and regenerative medicine by overcoming the limitations of the existing in vitro culture of human stem cells and providing comparable results for the stem cells of various genetic backgrounds which are capable of maintaining activity of aged cells.

Other features and aspects will be apparent from the following detailed description, drawings and claims.

Technical Solution

In one aspect of the present invention, there is provided a method for inducing high activity of human adipose stem cells, comprising culturing human mesenchymal stem cells in a medium containing a compound represented by the following Formula 1:

(1)

wherein $R_1$, $R_2$ and $R_3$ are independently H, $C_1$-$C_3$ alkyl or $C_1$-$C_4$ acyl.

The present inventors have made intensive studies to develop a method of stably obtaining mesenchymal stem cells which are the most valuable resources of cell therapeutic agents, and maintaining high activity of the same. As results, the present inventors have discovered that mesenchymal stem cells cultured in a medium containing the compound represented by the Formula 1 have greatly improved activity.

The present inventors have confirmed that the improved activity of adipose stem cells observed during coculture with adipocytes is owing to fat metabolites and identified that glycerol is the main constituent.

As used herein, the term "stem cell" refers to an undifferentiated cell that can differentiate without limitation into various cell types constituting the tissues of an organism so as to produce specialized cells of tissues and organs. The stem cells are totipotent or multipotent cells. The stem cell can divides either into two daughter stem cells or into one daughter stem cell and one original stem cell. Later, the cells proliferate into mature and complete cells of tissues.

As used herein, the term "mesenchymal stem cell" refers to a multipotent stem cell that can differentiate into adipocytes, osteocytes, chondrocytes, myocytes, neurons and cardiomyocytes. The mesenchymal stem cells are identified by the spiral shape and the expression of the surface markers CD73(+), CD105(+), CD34(−) and CD45(−).

As used herein, the term "high activity" refers to a state of superior maintenance of the differentiation potency of stem cells as well as high viability during in vitro culture. The highly active stem cells induced by the method of the present disclosure show significantly improved result in tube formation experiments as compared to the control group, as well as suppressed differentiation into adipocytes and improved growth ability.

According to a preferred embodiment, $R_1$, $R_2$ and $R_3$ of the Formula 1 are H. The compound of the Formula 1 with all of $R_1$, $R_2$ and $R_3$ being H is glycerol. Glycerol is produced from fat degradation in adipocytes. The present inventors have found out that the activity of adipose stem cells can be greatly improved by adding glycerol.

According to a preferred embodiment, the compound represented by the Formula 1 is included in the medium at a concentration of 1-100 μM.

According to a preferred embodiment, the medium further comprises a serum. The serum included in the medium is used to provide the effect known in the art. It plays an important role as source of growth factors in proliferation of the mesenchymal stem cells. Preferably, the serum may be, but not limited to, fetal bovine serum (FBS), bovine calf serum (BCS), horse serum or human serum, and more preferably, FBS.

As used herein, the term "medium" refers to a medium for animal cells commonly used in the art. The medium that can be used in the present disclosure may be any medium commonly used for culturing of animal cells. For example, Eagle's minimum essential medium (MEM) (Eagle, H. *Science* 130:432 (1959)), α-MEM (Stanner, C. P. et al., *Nat. New Biol.* 230:52 (1971)), Iscove's MEM (Iscove, N. et al., *J. Exp. Med.* 147:923(1978)), 199 medium (Morgan et al., *Proc. Soc. Exp. Bio. Med.*, 73:1 (1950)), CMRL 1066 and RPMI 1640 (Moore et al., *J. Amer. Med. Assoc.* 199:519 (1967)), F12 (Ham, *Proc. Natl. Acad. Sci. USA* 53:288 (1965)), F10 (Ham, R. G. *Exp. Cell Res.* 29:515 (1963)), Dulbecco's modified Eagle's medium (DMEM; Dulbecco, R. et al., *Virology* 8:396 (1959)), a mixture of DMEM and F12 (Barnes, D. et al., *Anal. Biochem.* 102:255 (1980)), Waymouth's MB752/1 (Waymouth, C. *J. Natl. Cancer Inst.* 22:1003 (1959)), McCoy's 5A (McCoy, T. A., et al., *Proc. Soc. Exp. Biol. Med.* 100:115 (1959)), MCDB series (Ham, R. G. et al., *In Vitro* 14:11 (1978)), or the like may be used. Specifically, it may be selected from a group consisting of α-MEM, Eagle's MEM, Iscove's MEM, 199 medium, CMRL 1066, RPMI 1640, F12, F10, DMEM, Waymouth's MB752/1 and McCoy's 5A. Most specifically, α-MEM may be used.

According to a preferred embodiment, the serum is included in the medium in an amount of 4-30 wt %. More preferably, the serum is included in the medium in an amount of 5-15 wt %, and most preferably, about 10 wt %.

With the method of inducing high activity, the same results were obtained for stem cells of different genetic origins, which were confirmed through cell number, cell proliferation assay (BrdU assay) and change in cell morphology. The stem cells could be obtained in high yield through in vitro culture.

According to a preferred embodiment, the mesenchymal stem cells are adipose stem cells.

As used herein, the term "adipose stem cell" refers to a mesenchymal stem cell derived from the adipose tissue. The adipose-derived mesenchymal stem cells can more easily differentiate into adipocytes than other mesenchymal stem cells and are less likely to differentiate into osteocytes (Gerard Ailhaud, *Biochemi and Biophys Res Commun.* 315(2): 255-263 (2004); Sakaguchi Y., *Arthritis Rheum.* 52(8) 2521-9 (2005)).

The adipose stem cells are isolated form the adipose tissue. The adipose tissue may be obtained from an animal by any known method. The adipose tissue may be isolated from an animal either alive or dead as long as the adipose stromal cells are viable. Typically, human adipose tissue is obtained from a living donor using well-recognized protocols, e.g., surgical or suction lipectomy. Specifically, the human adipose tissue may be obtained by excision or liposuction procedures well known in the art. The adipose-derived stem cells of the present disclosure are present in the initially excised or extracted adipose tissue, regardless of the method by which the adipose tissue is obtained.

In another aspect of the present invention, there is provided a method for inducing high activity of human adipose stem cells, comprising coculturing human mesenchymal stem cells with human adipocytes.

As used herein, the term "coculturing" refers to culturing two or more different types of cells together in the same space under the same culturing condition. The present inventors have confirmed that the function of adipose stem cells is improved by fat metabolites when the adipose stem cells are cocultured with adipocytess. Accordingly, the present disclosure may provide an efficient culturing method of superior viability of adipose stem cells and maintainability of differentiation potency.

As used herein, the term "human adipocytes" refers to cells derived from human adipose tissue. The adipose tissue consists of white fat, yellow fat or brown fat and plays an important in primary metabolism. The adipose tissue consists of adipocytes and stroma. The adipose tissue is found in the whole body of an animal. For example, in a mammal, the adipose tissue is present in the omentum, bone marrow and subcutaneous space and around most organs. The human adipocytes used in the method of the present disclosure may be of autologous or allogeneic origin.

According to a preferred embodiment, the coculturing is performed in a medium comprising a serum.

Since the serum and the medium used to induce high activity are the same as described above, description thereof will be omitted to avoid unnecessary redundancy.

According to a preferred embodiment, the coculturing is performed for 1-72 hours, more preferably for 6-48 hours, and most preferably for 24-48 hours.

In another aspect of the present invention, there is provided a highly active adipose stem cell obtained by the methods of the present invention. Since the highly active adipose stem cells can be obtained through culturing in a medium containing glycerol or through coculturing with adipocytes as described above, description thereof will be omitted to avoid unnecessary redundancy.

In another aspect of the present invention, there is provided a composition for forming adipocytes, osteocytes, chondrocytes, myocytes, neurons or cardiomyocytes, comprising the highly active mesenchymal stem cells.

The highly active stem cells induced by the method of the present disclosure may be used as a cell therapeutic agent for regenerating cells through differentiation of mesenchymal stem cells. More specifically, the composition of the present disclosure may be used as a composition for forming adipocytes, osteocytes, chondrocytes, myocytes, neurons or cardiomyocytes.

In another aspect of the present invention, there is provided a cell therapeutic agent comprising the highly active stem cells induced by the method of the present disclosure. Specifically, the cell therapeutic agent may be used to form adipocytes, osteocytes, chondrocytes, myocytes, neurons, cardiomyocytes, or the like.

As used herein, the term "cell therapeutic agent" refers to a drug for treatment, diagnosis or prevention of diseases, comprising cells or tissues prepared from humans via isolation, culturing and specialized manipulations (USFDA guidance), more particularly to a drug for treatment, diagnosis or prevention prepared by any process including proliferating or selecting autologous, homologous or heterologous cells ex vivo, or modifying the biological characteristics of cells, so as to restore the function of cells or tissues. Cell therapeutic agents are largely classified into somatic and stem therapeutic agents, and the present disclosure is particularly directed to the stem cell therapeutic agent.

When the composition of the present disclosure is prepared into a pharmaceutical composition, the pharmaceutical composition of the present disclosure comprises a pharmaceutically acceptable carrier. The pharmaceutically acceptable carrier included in the pharmaceutical composition of the present disclosure may be a commonly used one, including lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable carriers and formulations are described in detail in *Remington's Pharmaceutical Sciences* (19th ed., 1995).

The pharmaceutical composition according to the present invention may be administered orally or parenterally, and preferably, administered parenterally.

An appropriate administration dosage of the pharmaceutical composition of the present disclosure may be determined variously depending on such factors as preparation method, administration method, age, body weight and gender of a patient, pathological condition, diet, administration time, administration route, excretion rate or response sensitivity. A general dosage of the pharmaceutical composition of the present disclosure is $10^2$-$10^{10}$ cells per day for an adult.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

In another aspect of the present invention, there is provided a medium for inducing high activity of human mesenchymal stem cells, comprising a compound represented by the following Formula 1:

(1)

Wherein $R_1$, $R_2$ and $R_3$ are independently H, $C_1$-$C_3$ alkyl or $C_1$-$C_4$ acyl.

According to a preferred embodiment, $R_1$, $R_2$ and $R_3$ in the Formula 1 are H.

According to a preferred embodiment, the compound represented by the Formula 1 is included in the medium at a concentration of 1-100 μM.

According to a preferred embodiment, the medium further comprises a serum.

Since the serum and the medium used to induce high activity are the same as described above, description thereof will be omitted to avoid unnecessary redundancy.

In addition to the serum, the medium of the present disclosure may further comprise any ingredient known in the art for effective culture of the stem cells.

Advantageous Effects

The features and advantages of the present disclosure may be summarized as follows:

(a) The present invention provides a method for inducing high activity of human adipose stem cells, highly active stem cells induced by the method, cell therapeutic agents including the highly active stem cells, and a medium for inducing high activity of human adipose stem cells.

(b) According to the present disclosure, mesenchymal stem cells which are the best resource of cell therapeutic agents and supply of which is well established may be used, and high activity of human mesenchymal stem cells of various origins and different culture conditions can be induced broadly and systematically.

(c) The method of the present invention enables a long-term culture of human adipose stem cells while maintaining high activity, production yield and differentiation potency of the stem cells through in vitro culture.

DESCRIPTION OF DRAWINGS

FIG. 4 shows a result of excluding the effect by exposure to fat droplets. It was investigated whether the inducement of high activity of adipose stem cells occurring from coculture of the adipose stem cells with adipocytes is owing to fat. Since it is reported that the growth ability of stem cells increases under hypoxic environment, the effect of partial hypoxia caused by adipocytes was observed using a fat-exposed group and an adipose stem cells only group as controls. As seen from the figure, only the adipocyte-exposed group showed such effect.

MODE FOR INVENTION

The present disclosure will now be described in more detail through the following examples. The following examples are for illustrative purposes only and it will be obvious to those skilled in the art the scope of the present disclosure is not limited by the following examples.

Examples

Coculturing with Adipose Stem Cells

Human adipose tissue was sliced and digested for 30 minutes in a buffer solution containing 0.075% collagenase type 1 (Sigma-Aldrich, U.S.A.) to obtain single cells. After separating adipose stem cells and adipocytes from other tissue constituents by centrifugation, the human adipose stem cells were cultured in α-MEM (GIBCO®, Invitrogen Corporation, U.S.A.; containing L-glutamine, ribonucleoside and deoxyribonucleoside) containing 10% FBS. After repeated in vitro subculturing, the cells lose their fibroblast-like forms and become enlarged as they are aged. These cells do not grow any more. Those cells were seeded on a culture dish, $2 \times 10^4$ cells each, and, after stabilization for 24 hours, 500-1000 human adipocytes were added and coculturing was performed for 48 hours. Since it is reported that the growth ability of stem cells increases under hypoxic environment, the effect of partial hypoxia caused by adipocytes was excluded using a fat-exposed group as controls.

Culturing of Adipose Stem Cells in Medium Containing Glycerol

Through experiments to elucidate the mechanism of improved growth ability observed in coculturing with adipocytes, The present inventors have confirmed that the fat metabolite glycerol is one of the important factors and found out that the growth ability and differentiation efficiency can be enhanced only with glycerol, without adipocytes. The human adipose stem cells separated in vitro were cultured in α-MEM containing 10% FBS and 10-100 μM glycerol.

Characterization of High Activity-Induced Cells

1. Growth Ability (BrdU Assay)

DNA polymerization occurring during cell growth was quantitated using BrdU.

2. Analysis of Cell Cycle by Fluorescence-Activated Cell Sorting (FACS)

Cell cycle was analyzed by staining the nuclei of the separated cells.

3. Tube Formation Assay

Vascular tube formation ability was observed after coculturing the cells with human umbilical vein endothelial cells (HUVECs).

4. Analysis of Activation Mechanism

Figure 5:
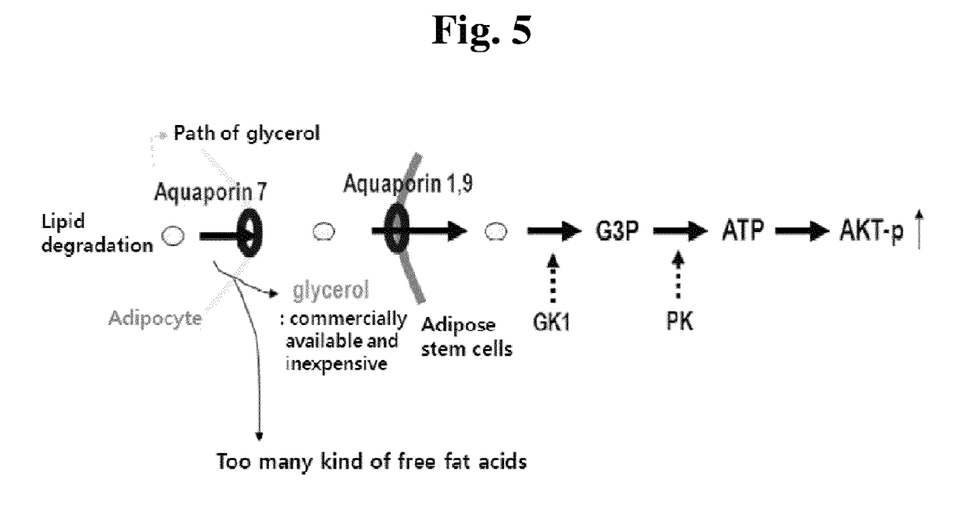
FIG. 5 is a schematic view illustrating a hypothesis for explaining the mechanism by which the activity of adipose stem cells increases when the adipose stem cells are cocultured with adipocytes. The present inventors have confirmed that glycerol and free fatty acids, which are fat metabolites, exist in the adipocytes and selected glycerol as a candidate of the active ingredient for increasing the activity of adipose stem cells.

A hypothesis was suggested to explain the mechanism by which the activity of the cells increases (FIG. 5). Expression of key factors was inhibited using siRNA (which specifically inhibits expression in the RNA level) for cells before and after activation. Then, protein was extracted from the cells of each group and the degree of AKT activation, which is a measure of cell activity, was measured. AKT (serine/threonine protein kinase) is well known as a cell activation marker in the field of cell biology. The degree of AKT activation is evaluated from the ratio of phosphorylated AKT (pAKT) to total AKT (tAKT). The total AKT was normalized with β-actin which is normally expressed in cells.

Figure 1:
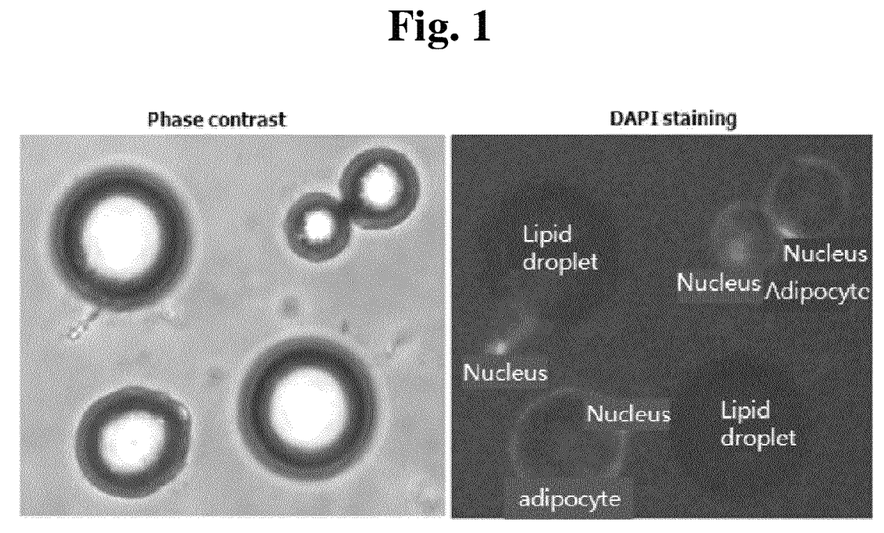
FIG. 1 shows a result of observing adipocytes isolated from human adipose tissue by phase contrast microscopy or DAPI staining.
Figure 2A:
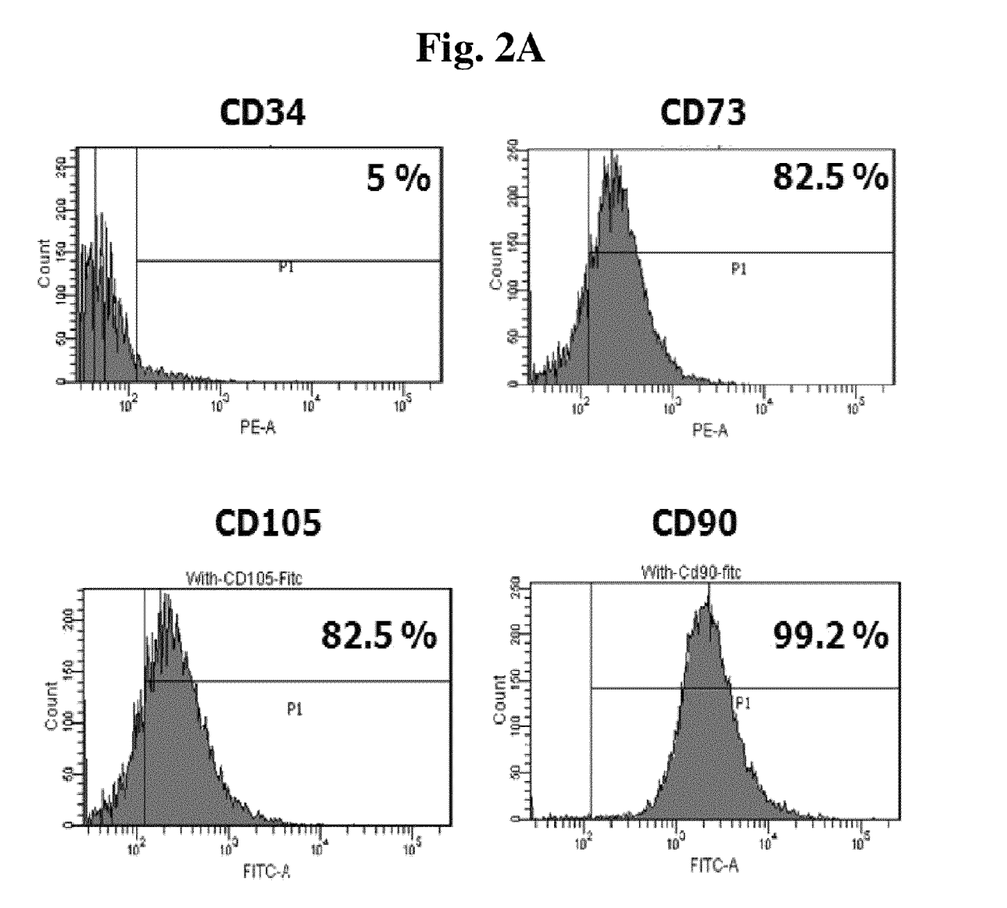
FIG. 2*a* shows a result of analyzing with cell markers. Cells were isolated from human adipose tissue and cultured for separation of mesenchymal stem cells. For cell identification, the cells showing the same morphology were stained with mesenchymal stem cell markers and analyzed by flow cytometry (FIG. 2a). When the mesenchymal stem cells stained with the markers were induced to differentiate into mesenchymal cells, they were identified as adipose-derived mesenchymal stem cells (FIG. 2b).
Figure 2B:
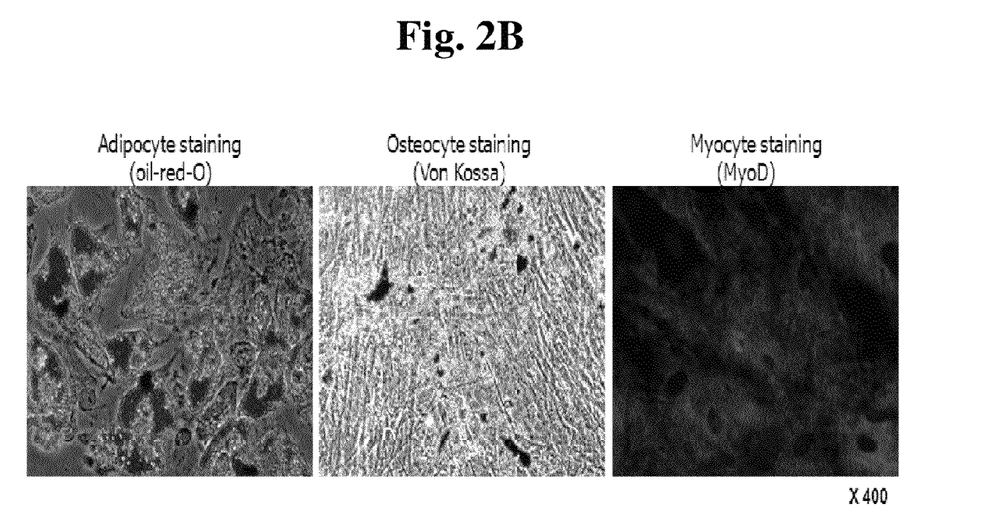
FIG. 2 shows a result of identifying adipose stem cells.
Figure 3A:
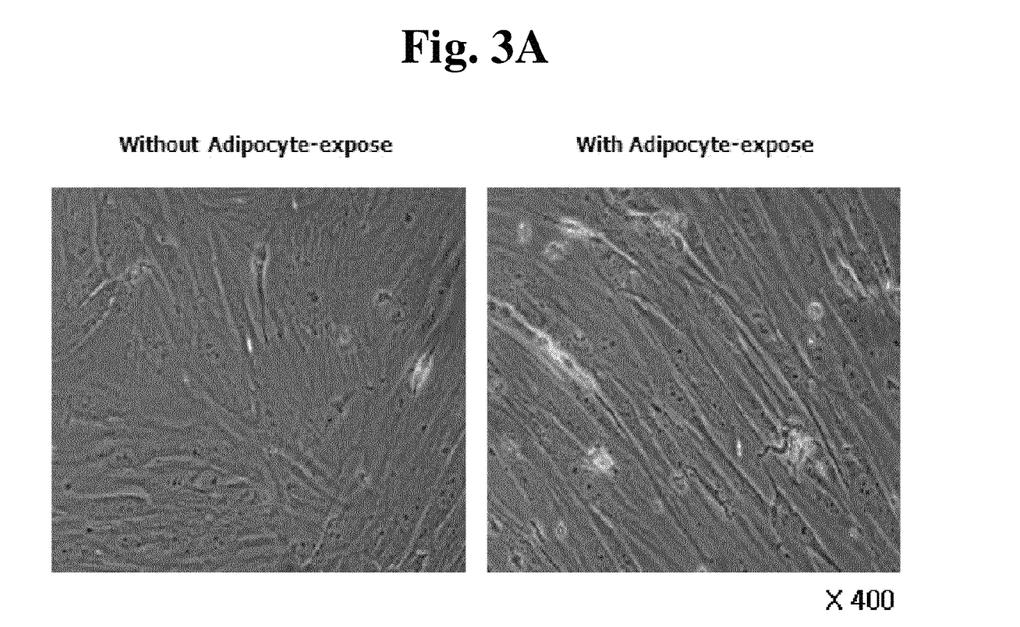
FIG. 3 shows a result of observing change in adipose stem cells after coculturing the adipose stem cells with adipocytes. Adipocytes and adipose stem cells were isolated from human adipose tissue and the adipocytes were removed after coculturing for 48 hours. To compare the cell morphology of the cells not cocultured (left) with that of the cells cocultured according to the method of the present disclosure (right), the cells of the control group lose their fibroblast-like forms and are enlarged, whereas the cells of the test group show fibroblast-like forms and fill the culture dish completely exhibiting the fingerprint pattern characteristic of healthy stem cells (FIG. 3a). The adipose stem cells cocultured with the adipocytes according to the method of the present disclosure showed increase of the S-phase with active proliferation ability from 5.44% to 12.99% (FIG. 3b).
Figure 3B:
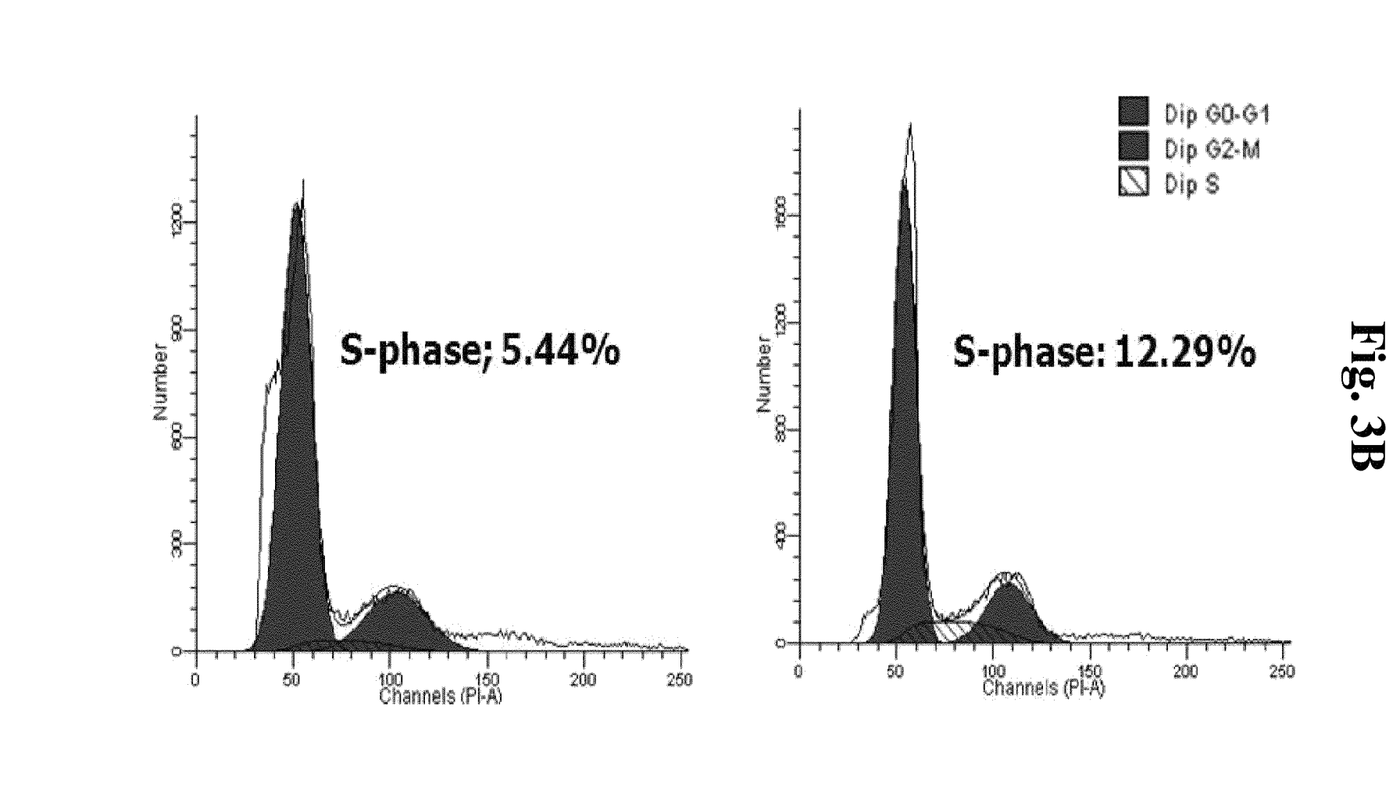
Figure 4:
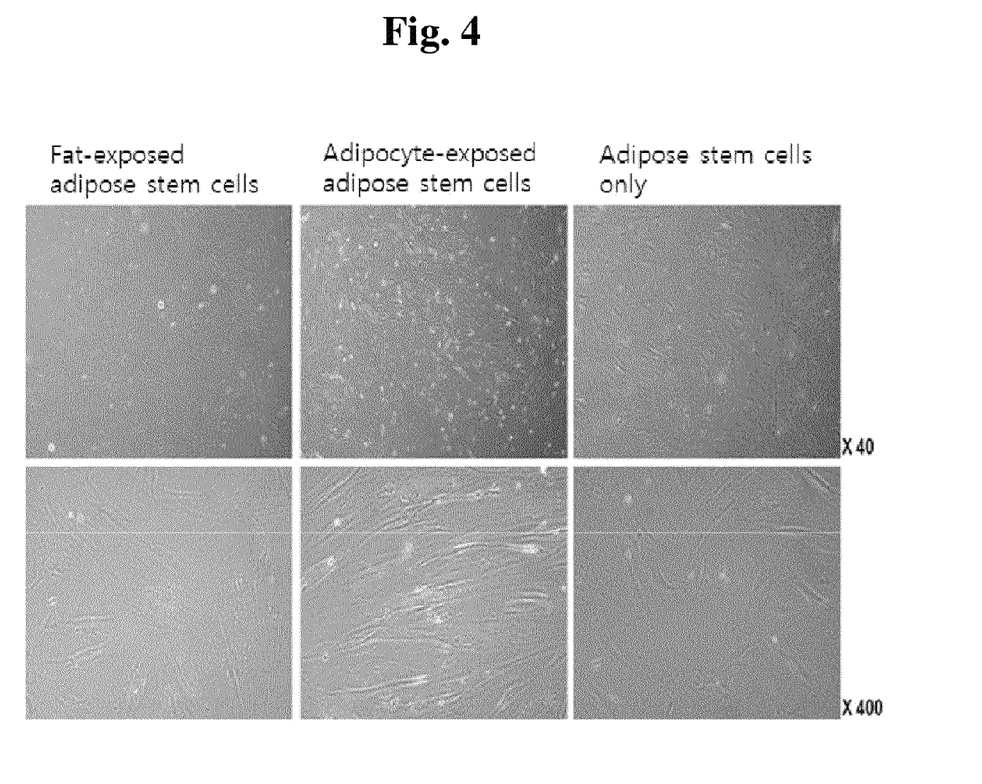

Inducement of High Activity of Human Adipose stem Cells by Coculturing with Human Adipocytes Human adipocytes were isolated and cocultured with aged human adipose stem cells in vitro in α-MEM containing 10% FBS for less than 48 hours. After 48 hours, the adipocytes died rapidly, resulting in increased fat vacuoles. The improved growth ability of the adipose stem cells was confirmed with cell morphology, cell number and cell cycle (FIG. 3). In FIG. 3a, to compare the cell morphology of the cells not cocultured (left) with that of the cells cocultured according to the method of the present disclosure (right), the cells of the control group lose their fibroblast-like forms and are enlarged, whereas the cells of the test group show fibroblast-like forms and fill the culture dish completely exhibiting the fingerprint pattern characteristic of healthy stem cells. This means that the growth ability of the adipose stem cells was enhanced. Also, as seen from FIG. 3b, the adipose stem cells cocultured with the adipocytes according to the method of the present disclosure showed increase of the S-phase with active proliferation ability from 5.44% to 12.99%. This means that the method of the present disclosure allows for better self-regeneration ability and active proliferation of the cells. Since it is reported that the growth ability of stem cells increases under hypoxic environment, the effect of partial hypoxia caused by adipocytes was observed using a fat-exposed group and an adipose stem cells only group as controls. As seen from FIG. 4, only the adipocyte-exposed group showed such effect.

Figure 6A:
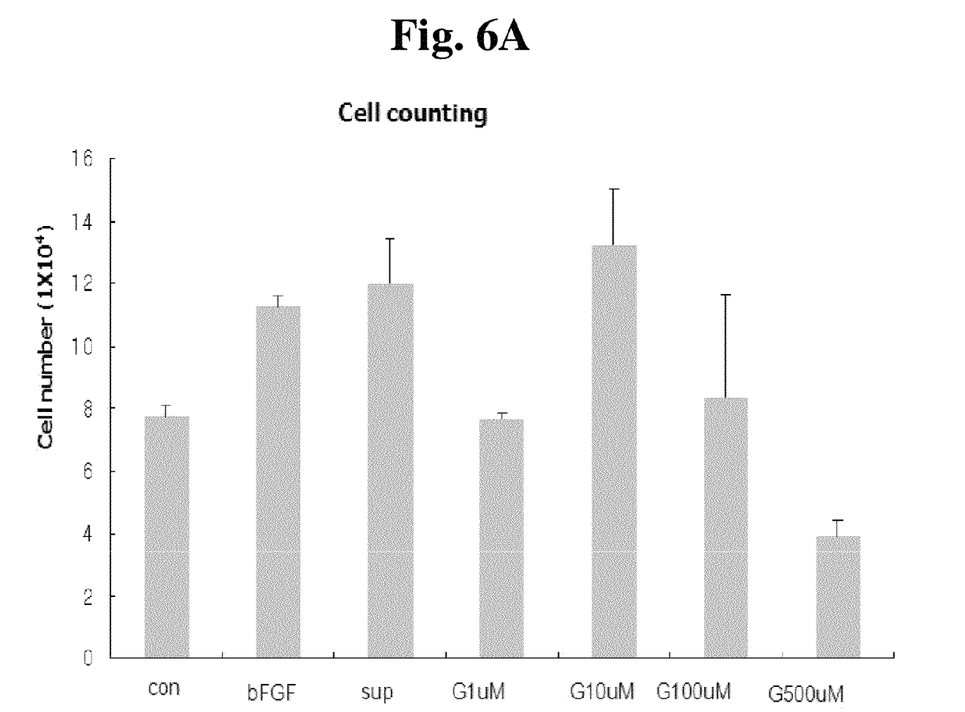
FIG. 6 shows that cell number increases when adipose stem cells are cultured in a medium containing glycerol. The cell number increased in a glycerol concentration-dependent manner (FIG. 6a). Further, the increase of cell number with glycerol concentration was confirmed from the observation of increased BrdU incorporation owing to cell division (FIG. 6b). In addition, the increase of cell number and morphological change with glycerol concentration were observed under a microscope (FIG. 6c). As a result, it was found out that 10 μM is the most effective glycerol concentration. bFGF and sup (adipocytes only) are control groups.
Figure 6B:
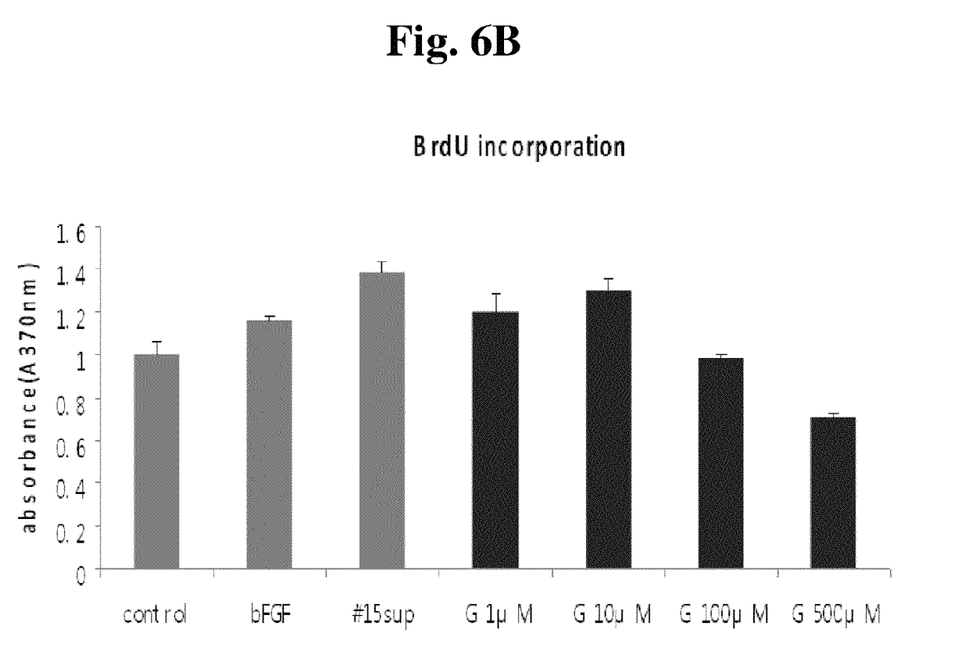
Figure 6C:
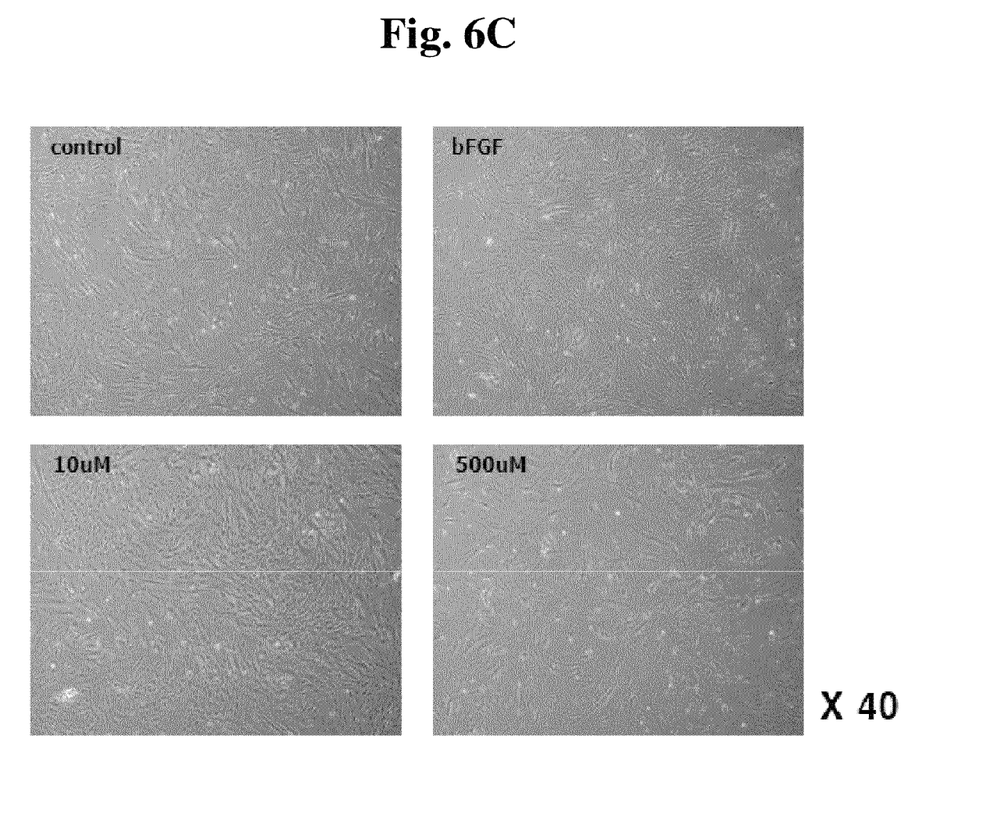

Inducement of High Activity of Human Adipose Stem Cells by Culturing in Medium Containing Glycerol The same number of isolated human adipose stem cells ($2 \times 10^4$ cells each) were cultured in a culture dish in α-MEM containing 10-100 μM glycerol and 10% FBS. Then, the improvement of the growth ability of the adipose stem cells was confirmed through cell counting and BrdU assay. As seen from FIG. 6a, among the groups to which the method of the present disclosure was applied, "G10 (10 μM glycerol)" showed a cell number larger than those of the negative control group "control" and the positive control group "bFGF (4 ng/mL)", suggesting that the highly active cells have enhanced growth ability. In addition, the degree of DNA polymerization was evaluated by BrdU assay in order to further investigate the ability of cell growth and differentiation. As a result, "G1" and "G10" to which the method of the present disclosure was applied showed active DNA synthesis (FIG. 6b). This indicates that the highly active cells induced by the method of the present disclosure have improved growth ability. But, cytotoxicity was observed when the glycerol concentration was higher (500 μM).

Figure 8:
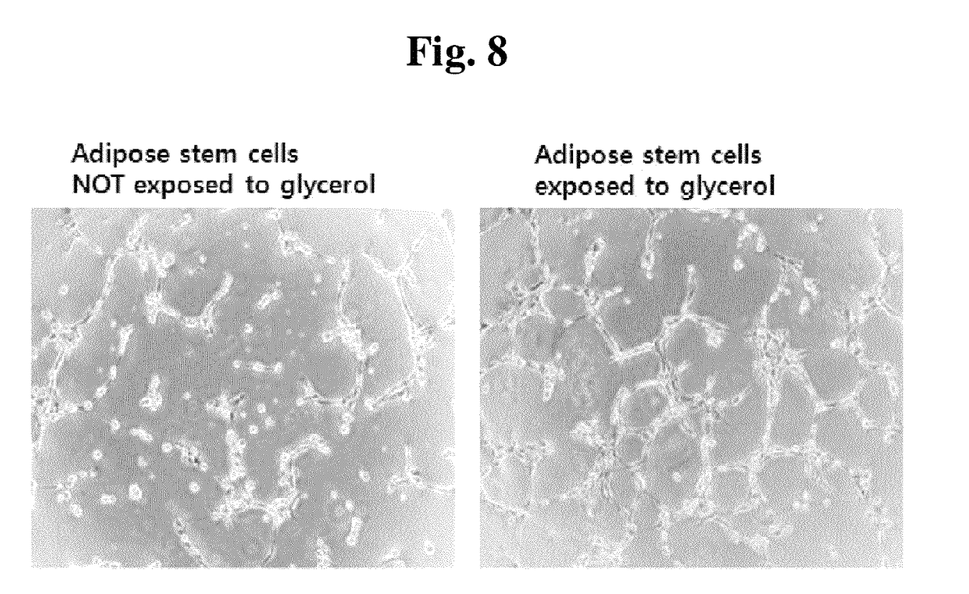
FIG. 8 shows a result of observing the increased vascular tube formation ability of highly active adipose stem cells induced by the method of the present disclosure using a phase contrast fluorescence microscope after coculturing with HUVECs. The left panel shows the result for the adipose stem cells not exposed to glycerol, and the right panel shows the result for the adipose stem cells exposed to glycerol. The exposure to glycerol resulted in increased vascular structures and densities.

Differentiation potency was evaluated by Matrigel tube formation assay, which is widely used to compare formation of capillary-like structures in vitro, after coculturing human adipose stem cells with HUVECs. As seen from FIG. 8, the highly active cells induced by the method of the present disclosure showed more capillary-like structures and hexagonal networks as compared to other groups. This means that the method of the present disclosure enhances vascular tube formation ability (FIG. 8).

Activation Mechanism of Human Adipose Stem Cells in Medium Containing Glycerol

Figure 7:
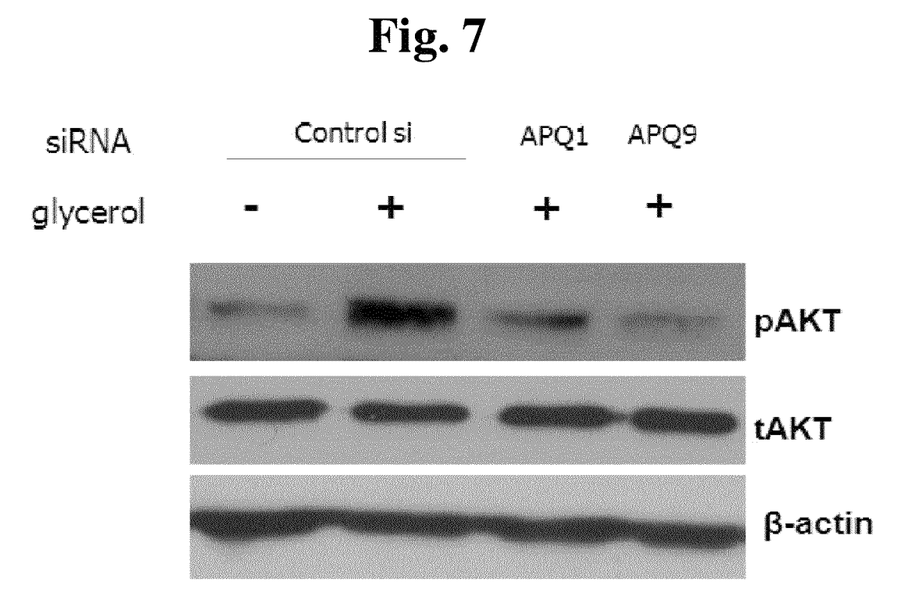
FIG. 7 shows a result of an experiment for testing the hypothesis of FIG. 5. Glycerol resulted in increased AKT activity, which was decreased again by inhibition of aquaporins (AQ1 and AQ9).

In order to test the hypothesis of FIG. 5, analysis was performed as shown in FIG. 7. Through the analysis, it was confirmed that glycerol activates the cells via aquaporin→AKT. As seen from FIG. 7, glycerol resulted in increased AKT activity, which was decreased again by inhibition of aquaporins. This suggests that the key factor of the coculturing is glycerol and confirms the suggested activation mechanism. Among many aquaporins, the inventors selected aquaporins 1 and 9 (AQ1 and AQ9) which had never been reported experimentally in this regard.

What is claimed is:

1. A method for inducing high activity of human mesenchymal stem cells, the method comprising culturing human mesenchymal stem cells in a medium containing a compound represented by the following Formula 1 at a concentration of 1-100 μM:

(1)

wherein $R_1$, $R_2$ and $R_3$ are H, $C_1$-$C_3$ alkyl or $C_1$-$C_4$ acyl.

2. The method according to claim 1, wherein the medium further comprises a serum.

3. The method according to claim 2, wherein the serum is selected from the group consisting of fetal bovine serum (FBS), bovine calf serum (BCS), horse serum, and human serum.

4. The method according to claim 1, wherein the medium is selected from the group consisting of α-MEM, Eagle's MEM, Iscove's MEM, 199 medium, CMRL 1066, RPMI 1640, F12, F10, DMEM, Waymouth's MB752/1 and McCoy's 5A.

5. The method according to claim 2, wherein the serum is included in the medium in an amount of 4-30 wt %.

6. The method according to claim 1, wherein the mesenchymal stem cells are adipose stem cells.

* * * * *